(12) United States Patent
Tategaki et al.

(10) Patent No.: US 9,750,775 B2
(45) Date of Patent: Sep. 5, 2017

(54) LACTIC ACID BACTERIUM-CONTAINING PREPARATION

(71) Applicant: Kaneka Corporation, Osaka-shi, Osaka (JP)

(72) Inventors: Airo Tategaki, Takasago (JP); Toyoaki Watanabe, Takasago (JP); Kazuya Hamada, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 14/707,521

(22) Filed: May 8, 2015

(65) Prior Publication Data

US 2015/0238547 A1 Aug. 27, 2015

Related U.S. Application Data

(62) Division of application No. 13/583,441, filed as application No. PCT/JP2011/055481 on Mar. 9, 2011, now abandoned.

(30) Foreign Application Priority Data

Mar. 10, 2010 (JP) .................................. 2010-053517
Nov. 19, 2010 (JP) .................................. 2010-259124

(51) Int. Cl.
| | | |
|---|---|---|
| A61K 35/74 | (2015.01) |
| A61P 3/06 | (2006.01) |
| A61K 35/744 | (2015.01) |
| C12R 1/01 | (2006.01) |
| A23L 33/10 | (2016.01) |
| A23L 33/135 | (2016.01) |
| C12N 1/20 | (2006.01) |

(52) U.S. Cl.
CPC ............ *A61K 35/744* (2013.01); *A23L 33/10* (2016.08); *A23L 33/135* (2016.08); *C12R 1/01* (2013.01); *A23V 2002/00* (2013.01); *A23Y 2280/15* (2013.01)

(58) Field of Classification Search
None
See application file for complete search history.

(56) References Cited

U.S. PATENT DOCUMENTS

| | | | | |
|---|---|---|---|---|
| 2003/0040475 | A1* | 2/2003 | Toba ....................... | A21D 2/263 424/535 |
| 2009/0010892 | A1* | 1/2009 | Masuda .................. | A61K 35/74 424/93.4 |
| 2009/0035288 | A1 | 2/2009 | Albers et al. | |
| 2009/0232785 | A1 | 9/2009 | Breton et al. | |

FOREIGN PATENT DOCUMENTS

| | | |
|---|---|---|
| CN | 1927022 A | 3/2007 |
| CN | 101172118 A | 5/2008 |
| CN | 101262779 A | 9/2008 |
| JP | 6057657 A | 3/1994 |
| JP | 2009-002959 | 7/1997 |
| JP | 10-298083 A | 11/1998 |
| JP | 2002-241292 A | 8/2002 |
| JP | 3585487 B1 | 11/2004 |
| JP | 2007-070249 A | 3/2007 |
| JP | 2007-302628 A | 11/2007 |
| JP | 2008-054556 A | 3/2008 |
| JP | 2008-178398 A | 8/2008 |
| JP | 2009-067742 A | 4/2009 |
| JP | 2009-521406 A | 6/2009 |

OTHER PUBLICATIONS

Quilty-Harper "The world's fattest countries: how do you compare?" The Telegraph, published online Jun. 21, 2012.*
International Preliminary Report on Patentability and Written Opinion dated Oct. 2, 2012 issued in corresponding Appln No. PCT/JP2011/055481.
Ayumi, A New Strategic Focus for Probiotics, Journal of Clinical and Experimental Medicine, 2003, vol. 207, No. 10, pp. 811-814.
Nguyen, et al., Characterization of Lactobacillus Plantarum PH04, A Potential Probiotic Bacterium With Cholesterol-lowering Effects, International Journal of Food Microbiology, 2007, vol. 113, pp. 358-361.
Bhathena, et al., Orally Delivered Microencapsulated Live Probiotic Formulation Lowers Serum Lipids in Hypercholesterolemic Hamsters, Journal of Medicinal Food, 2009, vol. 12, No. 2, pp. 310-319.
Miyao, S., et al., Series Commentary: Use of microorganisms and enzymes in Food Processing, Food & Packaging, 2007, vol. 48, No. 6, pp. 316-323.
Chafai et al., "Effects of pediococcus acidilactici feed supplementation on broiler chicken performances, immunity and health", Proceedings of the 16th European Symposium Poultry Nutrition: 281-284, 2007.

* cited by examiner

Primary Examiner — Emily Cordas
(74) Attorney, Agent, or Firm — Polsinelli PC

(57) ABSTRACT

The present invention provides very safe lactic acid bacteria and lactic acid bacteria preparations which are effective in prevention and therapy of allergies and/or in lowering of the blood neutral fat level. The present invention also provides pharmaceutical products and food or drink products which contain, as an active ingredient, a composition that contains cultured cells of the lactic acid bacterium *Pediococcus acidilactici* R037 or a treated product thereof.

9 Claims, 1 Drawing Sheet

LACTIC ACID BACTERIUM-CONTAINING PREPARATION

CROSS REFERENCE TO RELATED APPLICATIONS

This application is a Divisional of U.S. application Ser. No. 13/583,441 filed on Sep. 7, 2012, which is a National Phase filing under 35 U.S.C. §371 of PCT/JP2011/055481 filed on Mar. 9, 2011; and this application claims priority to Application No. 2010-053517 filed in Japan on Mar. 10, 2010 under 35 U.S.C. §119; and this application claims priority to Application No. 2010-259124 filed in Japan on Nov. 19, 2010 under 35 U.S.C. §119; the entire contents of all are hereby incorporated by reference.

TECHNICAL FIELD

The present invention relates to a novel lactic acid bacterium, and a preparation containing, as an active ingredient, cells of the lactic acid bacterium or a treated product thereof.

BACKGROUND ART

Changes in the living environment such as the Westernized diet, changed home environment, lack of exercise, and high stress levels in recent years have led to a trend of annual increases in the numbers of individuals suffering from and at high risk of what are now called "national diseases" such as allergic diseases and lifestyle diseases.

The number of individuals suffering from allergic diseases, particularly hay fever and atopic dermatitis disease, is ever increasing, and thus there is a strong desire for preventive and therapeutic measures against these diseases.

Hay fever and atopic dermatitis are classified as the group I allergic diseases which start with the recognition of a substance introduced into the body as an allergen and subsequent induction of the production of IgE antibody. When the allergen is reintroduced, the allergen binds to IgE antibodies that have become bound to receptor molecules on mast cells and granulocytes. As a result, the mast cells and granulocytes excessively release chemical mediators such as histamine and leukotriene, which causes allergy symptoms such as asthma, dermatitis, and nasal discharge.

For remedy of such allergic diseases, agents such as antihistamine agents and steroidal agents have been administrated as a symptomatic treatment. At present, however, side effects are seen with these drugs and there are also found safety issues regarding their methods of use and their long-term use.

Hyperlipidemia which is one of the lifestyle diseases, is indicated by a neutral fat level exceeding the reference value, and may be caused by the accumulation of unfavorable lifestyle habits such as unbalanced diet, lack of exercise, alcohol drinking, and smoking. It is considered that effective methods for lowering the neutral fat level are diet therapy and exercise therapy, but it is difficult to patiently continue these therapies. For this reason, methods of lowering the neutral fat level without mental and physical pains are desired.

Meanwhile, some of fermented foods produced using lactic acid bacteria have been drawing attention for their health effects such as intestinal regulation effects, immunostimulatory effects, and effects of preventing lifestyle diseases. For example, in the case of yogurt, the lactic acid bacteria cells used for fermentation and the milk peptides in the fermented milk have been reported to exhibit health effects as described above. The functions of lactic acid bacteria which are drawing attention today are the antiallergic function (Patent Literatures 1, 2), the neutral fat-lowering function (Patent Literatures 3, 4) and the like.

In Patent Literature 2, *Lactobacillus paracasei* KW3110 (FERM BP-08634) is reported to have a particularly high antiallergic function, but there is no report that lactic acid bacteria belonging to the genus *Pediococcus* have an antiallergic effect. In addition, although Patent Literature 4 reports that lactic acid bacteria belonging to the genus *Pediococcus* have a neutral fat-lowering effect, the effect does not seem to be sufficient yet.

Also, cocktails produced using functional lactic acid bacteria preparations are known to exhibit various health effects such as intestinal regulation effects when they are taken, but there are a few lactic acid bacteria preparations known to exhibit multiple functions.

CITATION LIST

Patent Literature

Patent Literature 1: JP H09-2959 A
Patent Literature 2: JP 3585487 B
Patent Literature 3: JP H10-298083 A
Patent Literature 4: JP H06-57657 B

SUMMARY OF INVENTION

Technical Problem

The present invention aims to provide very safe lactic acid bacteria that have at least one of an antiallergic function, a blood neutral fat-lowering function, and an anti-autoimmune disease function. The present invention also aims to provide preparations which contain a lactic acid bacterium having at least one of an antiallergic function, a neutral fat-lowering function, an anti-autoimmune disease function and the like, or a component derived from the lactic acid bacterium.

Solution to Problem

The present inventors have made intensive studies to solve the above problems, and have found that specific lactic acid bacteria belonging to the genus *Pediococcus* and components derived from the lactic acid bacteria have at least one of an excellent antiallergic function, neutral fat-lowering function, and anti-autoimmune disease function, particularly both the antiallergic function and neutral fat-lowering function. Thereby, the present invention has been completed.

That is, one aspect of the present invention is a strain of *Pediococcus acidilactici* R037 (accession number NITE BP-900) or a variant of the strain R037 having at least one of an antiallergic function, a neutral fat-lowering function, and an anti-autoimmune disease function.

Another aspect of the present invention is a composition which includes cultured cells of the lactic acid bacterium or a treated product thereof. The composition can be used as a pharmaceutical product, health food, or dietary supplement for the prevention or amelioration of an allergy, the lowering of the blood neutral fat level, and/or the prevention or amelioration of an autoimmune disease.

Yet another aspect of the present invention is an antiallergic agent including the composition preferably as an active ingredient.

Yet another aspect of the present invention is a blood neutral fat-lowering agent including the composition preferably as an active ingredient.

Yet another aspect of the present invention is an anti-autoimmune disease agent including the composition preferably as an active ingredient.

Yet another aspect of the present invention is a food or drink product including the composition.

Yet another aspect of the present invention is a method for treating at least one of an allergic disease, hypertriglyceridemia, and an autoimmune disease, the method including administering the composition to a subject.

Advantageous Effects of Invention

The present invention can provide a composition that contains very safe lactic acid bacterial cells or a treated product thereof. The composition of the present invention can be used as at least one of a preventive or ameliorative agent for an allergy, a neutral fat-lowering agent, and a preventive or ameliorative agent for an autoimmune disease which are against the diseases regarded as national diseases today.

DESCRIPTION OF EMBODIMENTS

Figure 1:
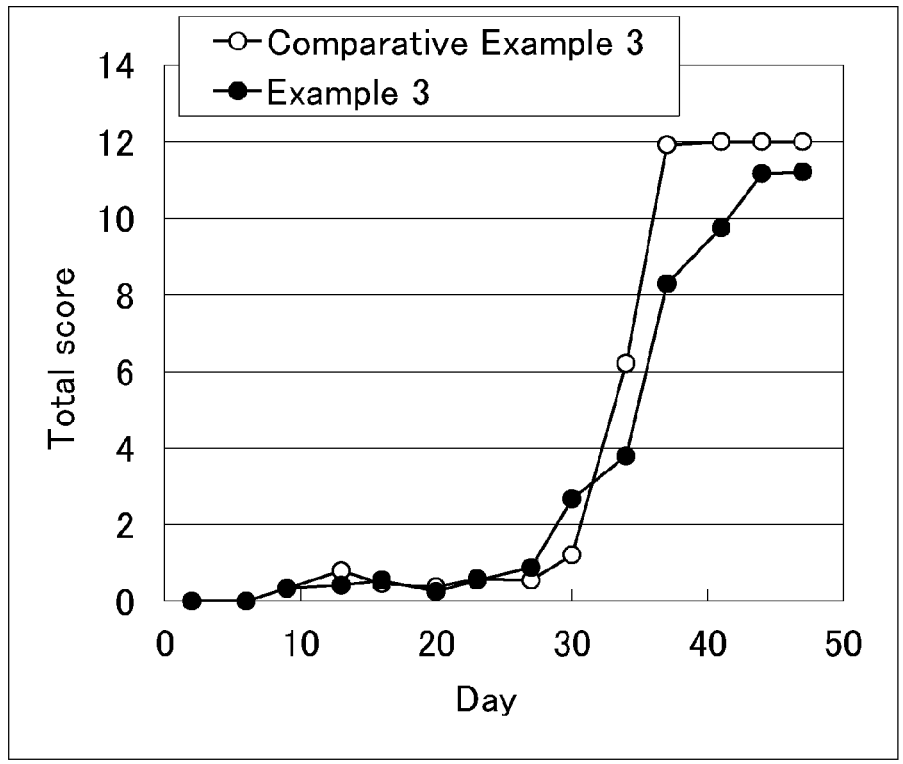
FIG. 1 is a view showing changes in the total dermatitis score of a mouse model of atopic dermatitis with and without administration of the lactic acid bacterium of the present invention.

Hereinafter, the present invention will be described in detail.

The lactic acid bacterium of the present invention, *Pediococcus acidilactici* R037 (hereinafter, also referred to as "the strain R037"), is a novel lactic acid bacterium isolated from fermented milk, and has been deposited with the Patent Microorganisms Depositary, Incorporated Administrative Agency National Institute of Technology and Evaluation (2-5-8 Kazusakamatari, Kisarazu-shi, Chiba, Japan) under the accession number NITE BP-900.

The strain R037 has the following bacteriological characteristics, and has been identified to be a strain belonging to *Pediococcus acidilactici*.

A. Morphological Characteristics
  1. Cell Form: Coccus
  2. Gram stain: Positive
  3. Sporulation: No
  4. Motility: No
B. Growing State on Culture Medium
  Colony morphology on MRS agar medium: White, circular, convex
C. Physiological Characteristics
  1. Growth ability at 37° C.: Positive
  2. Growth ability at 45° C.: Positive
  3. Catalitic reaction: Positive
  4. Fermentation of various carbohydrates (Positive: +, Negative: −)
    Arabinose: −
    Galactose: +
    Lactose: −
    Maltose: −
    Melezitose: −
    Ribose: +
    Xylose: +
D. Chemotaxonomic Characteristics The result of 16S rDNA sequence analysis shows that the base sequence of the strain R037 has an identity of 99.7% with that of *Pediococcus acidilactici* UL5.

As described in the examples below, the strain R037 has not only an excellent antiallergic/anti-atopic dermatitis function, but also an excellent neutral fat-lowering function.

The technical scope of the present invention encompasses not only the strain R037 but also variants thereof as long as they have equivalent functions, and the composition of the present invention may contain the variants in place of the strain R037. The variants are not particularly limited, and examples thereof include spontaneous variants, and variants obtained by artificially introducing mutations by known methods such as treatment with radiation or mutation-inducing substances.

Any culture medium can be used to culture the strain R037 or variants thereof, as long as they can grow in the culture medium. Examples of the culture method include, but not particularly limited to, test tube culture, flask culture, and fermentation tank culture. For example, the MRS medium generally used for lactic acid bacteria culture may be used and ordinary lactic acid bacteria culture may be carried out in this medium under generally used conditions.

The composition of the present invention contains cultured cells of the *Pediococcus acidilactici* R037 isolated from fermented milk, or a treated product thereof. The cells contained in the composition may be viable or dead (killed). Here, the viable cells refer to living lactic acid bacteria, and the dead (killed) cells refer to cells that have been subjected to a microbicidal treatment such as heat application, pressure application, and chemical treatment.

The composition of the present invention may not only contain the whole cell, but also may contain a treated product of the cells instead as long as the treated product has an equivalent function. The treated product of the cells herein refers to a liquid material obtained by, for example, grinding, disrupting, or extracting the lactic acid bacterial cells; or a treated product that has been subjected to at least one treatment selected from concentration, conversion into a paste, drying (e.g. spray drying, freeze drying, vacuum drying, drum drying), and dilution; or a residue from the extraction of the lactic acid bacteria.

Since the composition of the present invention containing the strain R037 of the present invention, a variant thereof, or a component derived from any of these lactic acid bacteria has an excellent antiallergic function, the composition can be used as an antiallergic agent. In a Th2-biased immune system, the antiallergic agent of the present invention functions to shift the immune response to antigen stimulation toward a Th1-type immune response, and can also limit the amount of production of IgE antibody. Accordingly, the antiallergic agent can prevent or ameliorate allergic diseases such as hay fever, atopic dermatitis, bronchial asthma, allergic rhinitis, and allergic conjunctivitis.

The antiallergic function in the present invention can be evaluated by, for example, culturing splenocytes from ovalbumin (OVA)-immunized BALB/c mice in a medium supplemented with OVA and the test substance, and measuring the cytokines (IL-12, IL-4) in the culture supernatant, as described below in the examples. The test substance is considered to have an antiallergic function if IL-12 production by the splenocytes is induced and IL-4 production is inhibited in the medium with the test substance, compared with the amounts of cytokines IL-12 and IL-4 produced by the splenocytes cultured in a medium without the test substance.

The antiallergic function can also be evaluated by administering the test substance orally to mice, immunizing the mice with OVA, and measuring the total IgE level in blood from these mice. The test substance is considered to have an antiallergic function if the total blood IgE level in these mice is reduced compared with that of mice not receiving the test substance.

The anti-atopic dermatitis function can be evaluated by, for example, administering the test substance to a mouse model of atopic dermatitis (SPF Nc/Nga mice), and treating the mice with picryl chloride so that the mice can be sensitized and induced to develop atopic dermatitis, as described below in the examples. The test substance is considered to have an anti-atopic dermatitis function if the dermatitis score of these mice is lower than that of mice not receiving the test substance.

The composition containing the strain R037, a variant thereof, or a component derived from any of these lactic acid bacteria has an excellent neutral fat-lowering function, and thus can be used also as a neutral fat-lowering agent. The neutral fat-lowering agent of the present invention lowers the neutral fat level in blood and controls the neutral fat concentration in blood serum to prevent or ameliorate lipid metabolism disorders and hypertriglyceridemia.

The neutral fat-lowering function can be evaluated by, for example, measuring the neutral fat level in blood serum of a mouse model of type 2 diabetes (KK-Ay mice), as described below in the examples. The test substance is considered to have a neutral fat-lowering function if the neutral fat level in blood serum of the mice is lower than that of mice not receiving the test substance.

The composition containing the strain R037, a variant thereof, or a component derived from any of these lactic acid bacteria has an excellent anti-autoimmune disease function, and thus can be used also as a preventive or ameliorative agent for an autoimmune disease. The autoimmune diseases mentioned herein refer to autoimmune diseases such as rheumatoid arthritis, systemic lupus erythematosus, Hashimoto's thyroiditis, and Crohn's disease.

The composition of the present invention can be used as a food, a functional food, a dietary supplement, a feed (e.g. pet foods), an animal drug, or a pharmaceutical product.

In the case that the composition of the present invention is consumed on an everyday basis as a food, the form of the food that contains the composition of the present invention is not particularly limited. Examples thereof include ordinary foods such as edible oil and fat compositions, cooking oils, spray oils, butters, margarines, shortenings, whipping creams, condensed milk products, whiteners, dressings, pickle liquids, breads, cakes, pies, cookies, Japanese confections, snack confections, fried confections, chocolate and chocolate confections, rice confections, rouxs, sauces, bastes, toppings, iced desserts, noodles, bakery mixes, fried foods, processed meat products, other processed food products (e.g., tofu, konjac food products), fish paste products, frozen foods (e.g., frozen entrees, frozen livestock food products, frozen agricultural foods), cooked rice, jams, cheeses, cheese foods, imitation cheese products, gums, candies, fermented milk products, canned goods, and beverages.

The amount of the lactic acid bacterium or a component derived from the lactic acid bacterium is not particularly limited in the case that the composition of the present invention is used as a food. The amount may be, for example, 0.00001 to 100% by weight, preferably 0.001 to 50% by weight, and more preferably 0.1 to 30% by weight, of the food.

In the case that the composition of the present invention is used as a functional food, a dietary supplement, a feed, or an animal drug, its dosage form is not particularly limited. Examples thereof include capsules, syrups, tablets, pills, powders, granules, drinks, injectables, transfusion fluids, nose drops, eye drops, suppositories, adhesive skin patches, and sprays. In formulation of a preparation, other pharmaceutically acceptable formulating agents, such as excipients, disintegrants, lubricants, binders, oxidation inhibitors, colorants, aggregation inhibitors, absorption promoters, dissolution auxiliaries, and stabilizers, can be suitably added. The preparation can be mixed into a compound feed or feed mixture, or can be suspended in drinking water before feeding. The composition of the present invention may also be just mixed with a feed before feeding.

In these cases, the composition of the present invention is administered in a single dose or multiple doses such that the daily intake of the lactic acid bacterium or a component derived from the lactic acid bacterium by the target animal, regardless of its species, is preferably 0.01 to 1000 mg/kg body weight per day, and more preferably 0.1 to 500 mg/kg body weight per day.

In the case that the composition of the present invention is used as a pharmaceutical product, its dosage form is not particularly limited. Examples thereof include capsules, syrups, tablets, pills, powders, granules, drinks, injectables, transfusion fluids, nose drops, eye drops, suppositories, adhesive skin patches, and sprays. In formulation of a preparation, other pharmaceutically acceptable formulating agents, such as excipients, disintegrants, lubricants, binders, oxidation inhibitors, colorants, aggregation inhibitors, absorption promoters, dissolution auxiliaries, and stabilizers, can be suitably added. The composition can also be prepared in the form of a dietary supplement (e.g. capsules, tablets) as a food with health claims (e.g. foods for specified health uses, foods with nutrient function claims) or a functional food (e.g. health foods, nutritional supplements), which may be labeled as a product for the prevention or amelioration of allergy symptoms, and/or the lowering of the neutral fat level. In these cases, the composition of the present invention is administered in a single dose or multiple doses such that the daily intake of the lactic acid bacterium or a component derived from the lactic acid bacterium by the target adult person is preferably 0.1 to 1000 mg/kg body weight per day, and more preferably 10 to 300 mg/kg body weight per day.

The composition of the present invention can be administered to a subject so as to prevent or ameliorate an allergic disease such as allergic or atopic dermatitis. The subject in this case is not particularly limited, and can be exemplified by individuals with allergic symptoms (e.g. allergic disease patients, atopic dermatitis patients); individuals currently without allergic symptoms but with a potential risk thereof found as a result of a test such as an antibody test; and healthy persons or healthy animals that should be prevented from developing allergic or atopic dermatitis or the like disease.

The composition of the present invention can be administered to a subject so as to lower the neutral fat level in blood. The subject in this case is not particularly limited, and can be exemplified by hypertriglyceridemia patients; individuals regarded as at high risk of hypertriglyceridemia because of their high neutral fat level as a result of a test such as a blood test; and healthy persons or healthy animals whose neutral fat level should be cared about because of their accumulation of unfavorable lifestyle habits.

The composition of the present invention can be administered to a subject so as to prevent or ameliorate an autoimmune disease. The subject to receive the composition for the prevention or amelioration of an autoimmune disease can be exemplified by individuals suffering from the diseases described above as examples of autoimmune diseases; individuals currently without the symptoms but with a potential risk thereof found as a result of a test such as an antibody test; and healthy persons or healthy animals that should be prevented from developing these diseases.

EXAMPLES

Hereinafter, the present invention will be more specifically described based on the examples which, however, are not intended to limit the scope of the present invention. In the examples, the antiallergic function, anti-atopic dermatitis function, and neutral fat-lowering function were evaluated by the following methods.

<Evaluation of Antiallergic Function>

Splenocytes from a mouse model of allergy (male BALB/c mice) that had been immunized with OVA antigen were co-cultured with OVA and the test substance. The antiallergic function was evaluated based on whether IL-4 production was inhibited and IL-12 production was promoted by this co-culture.

In addition, mice (male BALB/c mice) receiving the test substance orally were repeatedly immunized with OVA over a period of time, and the serum IgE was measured. The antiallergic function was then evaluated based on whether or not the increase in the serum IgE level in the mice receiving the test substance orally was inhibited compared with an increase with time in the serum IgE level in mice not receiving the test substance.

<Evaluation of Anti-atopic Dermatitis Function>

Picryl chloride was applied to the back and footpads of a mouse model of atopic dermatitis (SPF male Nc/Nga mice) that received the test substance orally, so as to sensitize the mice. Then, picryl chloride was applied to the back of and the right and left auricles of the mice so as to induce the mice to develop atopic dermatitis. The dermatitis score and auricular thickness of the mice were recorded. The anti-atopic dermatitis function was evaluated based on whether or not the increase with time in the dermatitis score and auricular thickness of the mice receiving the test substance orally was inhibited compared with an increase with time in the dermatitis score and auricular thickness of mice not receiving the test substance.

<Evaluation of Neutral Fat-lowering Function>

The neutral fat level in blood serum of a mouse model of type 2 diabetes (male KK-Ay mice) that received the test substance orally was measured. The neutral fat-lowering function was evaluated based on whether or not the increase in the neutral fat level in blood serum of the mice receiving the test substance orally was inhibited compared with an increase with time in the neutral fat level in blood serum of mice not receiving the test substance.

(Preparations 1 to 4) Preparation of Different Lactic Acid Bacteria

The lactic acid bacteria listed in Table 1 were each cultured for 48 hours in MRS medium (prepared by dissolving 52 g of MRS bouillon (Kanto Chemical Co., Inc.) in 1 L of water, and sterilizing the mixture by autoclaving for 15 minutes at 121° C.). After the culturing, the bacterial cells were collected by centrifugal separation, washed 3 times with sterilized water, dispersed in 20 ml of sterilized water, heated for 10 minutes at 80° C., and then freeze-dried, whereby freeze-dried cells 1 to 4 of the respective lactic acid bacteria were obtained.

TABLE 1

| | Lactic acid bacterial strain added |
|---|---|
| Preparation 1 (freeze-dried cells 1) | *Pediococcus acidilactici* R037 (accession number: NITE BP-900) |
| Preparation 2 (freeze-dried cells 2) | *Lactobacillus delbrueckii* subsp. *lactis* KR-188 (accession number: NITE P-396) |
| Preparation 3 (freeze-dried cells 3) | *Enterococcus durans* KR-211 (accession number: NITE P-397) |
| Preparation 4 (freeze-dried cells 4) | *Leuconostoc mesenteroides* subsp. *mesenteroides* KLAB-2 (accession number: NITE P-393) |

Example 1

Measurement of Antiallergic Function of Lactic Acid Bacteria by In Vitro Test

Five-week-old female BALB/c mice (from Charles River Japan) were used in this experiment after acclimation for one week. The BALB/c mice were intraperitoneally immunized with an antigen solution prepared by mixing 100 μg of OVA and 2 mg of aluminum hydroxide gel and diluting the mixture to 200 μL with physiological saline (primary immunization). After one week, the mice were intraperitoneally immunized again with the same amount of the antigen solution (secondary immunization). One week after the secondary immunization, the OVA-specific IgE antibody titer was measured by ELISA. The mice showing an increase in the antibody titer were taken as the mouse model of allergy.

Splenocytes were prepared from the allergic model mice, and were then suspended in RPMI 1640 medium (product name: RPMI 1640, from SIGMA®) which contained 10% fetal bovine serum, to give $2.0 \times 10^6$ cells/mL. OVA (1 mg/mL) for antigen stimulation and the dried lactic acid bacterial cells 1 (1 μg/mL) prepared in Preparation 1 were added to the medium. The splenocytes were then cultured for 7 days in a 5% $CO_2$ incubator at 37° C. After the culturing, the IL-4 and IL-12 present in the supernatant were measured by ELISA (product name: QUANTIKINE®, from R&D SYSTEMS®) and the measured values were used in the evaluation. The results are summarized in Table 2.

Reference Examples 1 to 3

Measurement of Antiallergic Function of Lactic Acid Bacteria by In Vitro Test

The antiallergic function of mice for reference examples was measured in the same manner as in Example 1, except that one of the dried lactic acid bacterial cells 2 to 4 was used. The results are summarized in Table 2.

Comparative Example 1

Measurement of Antiallergic Function of Lactic Acid Bacteria by In Vitro Test

The antiallergic function of mice as a negative control was measured in the same manner as in Example 1, except that no lactic acid bacteria solution was added and PBS (−) was used. The results are summarized in Table 2.

Reference Example 4

Measurement of Antiallergic Function of Lactic Acid Bacteria by In Vitro Test

The antiallergic function of mice as a positive control was measured in the same manner as in Example 1, except that no lactic acid bacteria solution was added and 1 μg/mL of the immunostimulant PICIBANIL™ (Chugai Pharmaceutical Co., Ltd.) which has an ability to activate Th1 was used. The results are summarized in Table 2.

Reference Example 5

Measurement of Antiallergic Function of Lactic Acid Bacteria by In Vitro Test

For comparison with Japanese Patent No. 3585487, dried lactic acid bacterial cells were prepared in the same manner as in Preparations 1 to 4, except that *Lactobacillus casei* L14 (Japan Dairy Technical Association, identical to *Lactobacillus paracasei* KW3110, FERM BP-08634), a lactic acid bacterium known as having antiallergic activity, was used in place of the lactic acid bacteria used in Preparations 1 to 4. Using the dried cells, the antiallergic function of mice as a positive control with the lactic acid bacterium was measured in the same manner as in Example 1. The results are summarized in Table 2.

production by about 2.5 times as much as that in Reference Example 5, and inhibited the IL-4 production to the extent of about half that in Reference Example 5, which indicates that the strain R037 has high antiallergic activity.

Example 2

Measurement of Antiallergic Function of Preparation by In Vivo Test

First, 0.05 parts by weight of the freeze-dried cells 1 of the strain R037 which had been prepared in Preparation 1 was thoroughly mixed with 0.45 parts by weight of an excipient (product name: PINEDEX #2™, from Matsutani Chemical Industry Co., Ltd.) to prepare a lactic acid bacteria preparation. An amount of 0.5 parts by weight of the prepared lactic acid bacteria preparation was mixed with 99.5 parts by weight of a powdered mouse feed (product name: CE-2, from Oriental Yeast Co., Ltd.) to provide a lactic acid bacteria preparation-supplemented feed that contained 0.5% by weight of the lactic acid bacteria preparation.

Five-week-old female BALB/c mice (from Charles River Japan) were acclimated for one week. After that, administration of the lactic acid bacteria preparation-supplemented feed was started (ad libitum intake of the lactic acid bacterium at approximately 2.5 mg/day on average). One week after the start day (i.e. on Day 7), the mice were intraperitoneally immunized with an antigen solution prepared by mixing 100 μg of OVA and 2 mg of aluminum hydroxide gel and diluting the mixture to 200 μL with physiological saline.

TABLE 2

| | Lactic acid bacterial strain added | (Unit: pg/ml) IL-4 | IL-12 |
|---|---|---|---|
| Example 1 (freeze-dried cells 1) | *Pediococcus acidilactici* R037 (accession number: NITE BP-900) | 145.1 | 449.8 |
| Reference Example 1 (freeze-dried cells 2) | *Lactobacillus delbrueckii* subsp. *lactis* KR-188 (accession number: NITE P-396) | 73.9 | 334.0 |
| Reference Example 2 (freeze-dried cells 3) | *Enterococcus durans* KR-211 (accession number: NITE P-397) | 105.6 | 306.6 |
| Reference Example 3 (freeze-dried cells 4) | *Leuconostoc mesenteroides* subsp. *mesenteroides* KLAB-2 (accession number: NITE P-393) | 39.6 | 356.5 |
| Comparative Example 1 | — | 3584.9 | — |
| Reference Example 4 | (Immunostimulant Picibanil)[1] | 434.5 | 253.1 |
| Reference Example 5 | *Lactobacillus casei* L14[2] | 313.4 | 172.8 |

[1]Chugai Pharmaceutical Co., Ltd., preparation which is not a lactic acid bacterium
[2]Identical to *Lactobacillus paracasei* KW3110 (FERM BP-08634), identified by Japan Dairy Technical Association Table 2 shows the amounts of IL-4 production and IL-12 production by splenocytes from the allergic model mice in the case of co-culture with the lactic acid bacteria and OVA. In Comparative Example 1 using no lactic acid bacteria, the OVA-stimulated splenocytes from allergic model mice exhibited a strong Th2-type immune response in which IL-4 production was induced and the amount of IL-12 production was below the detection limit. In contrast, in Reference Example 4 using PICIBANIL™, the OVA-stimulated splenocytes from allergic model mice exhibited a Th1-type immune response in which IL-4 production was inhibited and IL-12 production was induced. In addition, in Reference Example 5 using *Lactobacillus casei* L14, the splenocytes exhibited a Th1-type immune response as in Reference Example 4. The splenocytes in Example 1 and Reference Examples 1 to 3 also exhibited inhibition of IL-4 production and induction of IL-12 production. In particular, the results in Example 1 show that the strain R037 activated the IL-12

Immunization with the OVA antigen solution was similarly performed after 2 weeks (Day 14), after 4 weeks (Day 28), after 6 weeks (Day 42), and after 8 weeks (Day 56). In order to measure the total IgE level in blood, blood was collected from the mouse jugular vein after 3 weeks (Day 21), after 5 weeks (Day 35), after 7 weeks (Day 49), and after 9 weeks (Day 63). The serum was collected by centrifugal separation of the collected blood, and the total IgE level in the serum was measured using a YAMASA® IgE/EIA Kit (from Yamasa Corporation). The measured values are shown in Table 3.

Reference Examples 6 to 8

Measurement of Antiallergic Function of Preparation by In Vivo Test

The total IgE level in the collected serum was measured in the same manner as in Example 2, except that one of the freeze-dried lactic acid bacterial cells 2 to 4 (prepared in Preparations 2 to 4) was used in place of the freeze-dried bacterial cells of the strain R037. The measured values are shown in Table 3.

Comparative Example 2

Measurement of Antiallergic Function of Preparation by In Vivo Test

The total IgE level in the collected serum of mice as a negative control was measured in the same manner as in Example 2, except that a powdered mouse feed (product name: CE-2, from Oriental Yeast Co., Ltd.) was used without adding the lactic acid bacteria preparation, in place of the lactic acid bacteria preparation-supplemented feed. The measured values are shown in Table 3.

Reference Example 9

Measurement of Antiallergic Function of Preparation by In Vivo Test

For comparison with Japanese Patent No. 3585487, the total IgE level in the collected serum of mice as a positive control was measured in the same manner as in Example 2, except that a lactic acid bacteria-supplemented feed, which was prepared by mixing 99.925 parts by weight of the powdered mouse feed with 0.075 parts by weight of a health supplement containing *Lactobacillus paracasei* KW3110 (product name: NOALE CAPSULE™, from Kirin Yakult Nextstage Co., Ltd.), was used in place of the lactic acid bacteria preparation containing the freeze-dried cells 1. The measured values are shown in Table 3.

Here, no differences were seen in the mouse body weight and total amount of intake among the experiments in Example 2, Comparative Example 2, and Reference Examples 6 to 9.

a particularly high antiallergic function, even compared with the preparation of Reference Example 9. Since the changes in the total IgE level in these experiments are considered to correspond to the changes in the OVA-specific IgE level, the results demonstrated that the composition of the present invention has an antiallergic effect.

Example 3

Measurement of Anti-atopic Dermatitis Function of Preparation by In Vivo Test

An amount of 0.33 parts by weight of the freeze-dried cells 1 of the strain R037 prepared in Preparation 1 was mixed with 99.67 parts by weight of a powdered mouse feed (product name: CE-2, from CLEA Japan, Inc.) to prepare a lactic acid bacteria-supplemented feed that contained 0.33% by weight of the freeze-dried cells 1.

Seven-week-old SPF male Nc/Nga mice (from Charles River Japan) were acclimated for one week. After that, administration of the prepared lactic acid bacteria-supplemented feed was started (ad libitum intake of the lactic acid bacterium at approximately 17 mg/day on average). One day after the start day (i.e. on Day 1), the mice were placed under isoflurane anesthesia and 150 μL of a PiCl sensitizing solution (5% (w/v) PiCl solution (solvent: ethanol/acetone=4:1)) was applied to the shaved abdomen of and the footpads of the mice. The induction of atopic dermatitis was performed 4 days (Day 5) after the sensitization, by applying 150 μL of a PiCl induction solution (0.8% (w/v) PiCl solution (solvent: olive oil)) to the back of and the right and left auricles (both inside and outside) of the mice. This operation for atopic dermatitis induction was repeated every week, 7 times in total. The conditions of the skin were observed twice a week from the day on which the sensitization was started (Day 1). Based on the clinical evaluation

TABLE 3

| | Lactic acid bacteria mixed into feed | Day 0 | Day 21 | Day 35 | Day 49 | Day 63 (Unit: ng/ml) |
|---|---|---|---|---|---|---|
| Example 2 | *Pediococcus acidilactici* R037 (accession number: NITE BP-900) | 0 | 147 | 450 | 510 | 547 * |
| Reference Example 6 | *Lactobacillus delbrueckii* subsp. *lactis* KR-188 (accession number: NITE P-396) | 0 | 161 | 434 | 695 | 637 * |
| Reference Example 7 | *Enterococcus durans* KR-211 (accession number: NITE P-397) | 0 | 124 | 293 | 509 | 720 * |
| Reference Example 8 | *Leuconostoc mesenteroides* subsp. *mesenteroides* KLAB-2 (accession number: NITE P-393) | 0 | 155 | 561 | 784 | 790 * |
| Comparative Example 2 | — | 0 | 172 | 773 | 1105 | 1443 |
| Reference Example 9 | *Lactobacillus paracasei* KW3110 (product name: Noale Capsule, from Kirin Yakult Nextstage Co., Ltd.) | 0 | 105 | 481 | 618 | 706 * |

The asterisk * indicates that the value is significantly different from that of Comparative Example 2.

Figure 2:
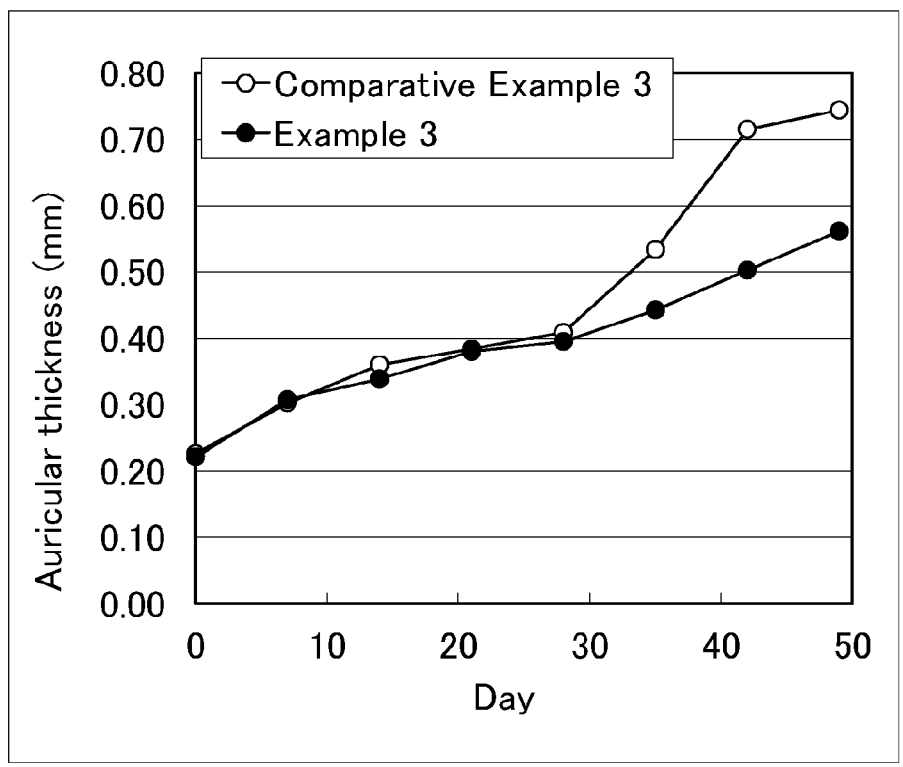
FIG. 2 is a view showing changes in the auricular thickness of a mouse model of atopic dermatitis with and without administration of the lactic acid bacterium of the present invention.

The results of Table 3 show the following facts. The total blood IgE level in the positive control group (Reference Example 9) on Day 63 was lower than that in the negative control group (Comparative Example 2) receiving a feed not supplemented with the lactic acid bacteria preparation. The total blood IgE level in the mice receiving the lactic acid bacteria preparation-supplemented feed in Example 2 and Reference Examples 6 to 8 on Day 63 was also lower than that in the control group in Comparative Example 2. The results in Table 3 show that the preparation containing the freeze-dried cells 1 of the strain R037 in Preparation 1 had standards for human atopic dermatitis, five items, i.e., itching, erythema/hemorrhage, edema, excoriation/erosion, scaling/dryness, were graded as follows: no symptoms (0 points); mild (1 point); moderate (2 points); and severe (3 points). The sum of points was regarded as the total dermatitis score and was used for evaluation. The auricular thickness was also measured once a week using a micrometer from the test start day (Day 0). The determined total dermatitis scores are shown in FIG. 1 and the measured auricular thicknesses are shown in FIG. 2.

Comparative Example 3

Measurement of Anti-atopic Dermatitis Function of Preparation by In Vivo Test

The total score and auricular thickness of mice as a negative control were determined in the same manner as in Example 3, except that a powdered mouse feed (product name: CE-2, from CLEA Japan, Inc.) was used without adding the freeze-dried lactic acid bacterial cells. The results are shown in FIGS. 1 and 2.

Here, no differences were seen in the mouse body weight and total amount of intake between the experiments in Example 3 and Comparative Example 3.

The results in FIGS. 1 and 2 show the following facts. The negative control group (Comparative Example 3) receiving a feed not supplemented with the lactic acid bacteria showed an increase in the total score and auricular thickness after the 4th atopic dermatitis induction. In contrast, the mouse group (Example 3) receiving a feed supplemented with the freeze-dried cells 1 of the strain R037 showed an inhibitory effect on the increase in the total score and auricular thickness; here, the increase was significantly inhibited on Day 34 and later regarding the total score, and on Day 35 and later regarding the auricular thickness. These results demonstrated that the composition of the present invention has an anti-atopic dermatitis function.

Example 4

Measurement of Neutral Fat-lowering Function of Preparation by In Vivo Test

First, a lactic acid bacteria preparation was prepared by mixing 67 parts by weight of the freeze-dried bacterial cells 1 of the strain R037 (prepared in Preparation 1) and 33 parts by weight of an excipient (product name: PINEDEX #2™, from Matsutani Chemical Industry Co., Ltd.). The lactic acid bacteria preparation was suspended in distilled water so as to give a lactic acid bacteria preparation-admixed liquid having a concentration of 10% by weight.

Eight-week-old male KK-Ay mice (from CLEA Japan, Inc.) were acclimated for two weeks on ad libitum intake of a mouse feed (product name: CE-2, from Oriental Yeast Co., Ltd.) and sterilized water. After that, the prepared lactic acid bacteria preparation-admixed liquid was forcibly administered every day using a plastic mouse-feeding needle and a 1-mL tuberculin syringe so that the amount of the liquid was 7.5 mL per kilogram of the mouse body weight per day (forcible administration of approximately 20 mg/day of the lactic acid bacteria).

During the period of the experiment, a mouse feed (product name: CE-2, from Oriental Yeast Co., Ltd.) and sterilized water were freely available to the mice. After two weeks of forcible administration without interruption, blood serum was collected from blood from the mice, and the neutral fat level in the serum was measured using a neutral fat measuring kit (TRIGLYCERIDE E-TEST WAKO™, from Wako Pure Chemical Industries, Ltd.). The measured value is shown in Table 4.

Comparative Example 4

Measurement of Neutral Fat-Lowering Function of Preparation by In Vivo Test

The neutral fat level in the collected serum of mice as a negative control was measured in the same manner as in Example 4, except that distilled water without the lactic acid bacteria preparation was used in place of the lactic acid bacteria preparation-admixed liquid. The measured value is shown in Table 4.

Reference Example 10

Measurement of Neutral Fat-lowering Function of Preparation by In Vivo Test

The neutral fat level in the collected serum of mice as a positive control was measured in the same manner as in Example 4, except that the lactic acid bacteria preparation-admixed liquid was replaced with a dilution obtained by diluting with distilled water Pioglitazone (from Takeda Pharmaceutical Co., Ltd.) which is a drug that improves insulin resistance and acts to lower the neutral fat level in blood serum, to give a concentration of 0.4% by weight. The measured value is shown in Table 4.

Reference Example 11

Measurement of Neutral Fat-lowering Function of Preparation by In Vivo Test

Freeze-dried cells were prepared in the same manner as in Preparation 1, using *Pediococcus acidilactici* JCM2032 (purchased from Independent Administrative Institution RIKEN BioResource Center) in place of the freeze-dried cells 1 of the strain R037. The neutral fat level in the collected serum was then measured in the same manner as in Example 4. The measured value is shown in Table 4.

Reference Example 12

Measurement of Neutral Fat-lowering Function of Preparation by In Vivo Test

Freeze-dried cells were prepared in the same manner as in Preparation 1, using *Pediococcus acidilactici* JCM8797 (purchased from Independent Administrative Institution RIKEN BioResource Center) in place of the freeze-dried cells 1 of the strain R037. The neutral fat level in the collected serum was then measured in the same manner as in Example 4. The measured value is shown in Table 4.

Reference Example 13

Measurement of Neutral Fat-lowering Function of Preparation by In Vivo Test

The neutral fat level in the collected serum was measured in the same manner as in Example 4, except that the lactic acid bacteria preparation-admixed liquid was replaced with a lactic acid bacteria suspension obtained by suspending in distilled water a health supplement containing *Lactobacillus paracasei* KW3110 (product name: NOALE CAPSULE™, from Kirin Yakult Nextstage Co., Ltd.) to give a concentration of 10% by weight. The measured value is shown in Table 4.

No differences were found in the mouse body weight and total amount of intake among the experiments in Example 4, Comparative Example 4, and Reference Examples 10 to 13.

TABLE 4

| | Neutral fat level in blood serum (mg/dl) |
|---|---|
| Example 4 | 360.1 |
| Comparative Example 4 | 596.6 |
| Reference Example 10 | 359.8 |
| Reference Example 11 | 495.2 |
| Reference Example 12 | 477.3 |
| Reference Example 13 | 463.3 |

The results in Table 4 show the following facts. The neutral fat level in blood serum of the mice in Reference Example 10 (the mice were forcibly administered neutral fat-lowering Pioglitazone) was lower than the neutral fat level in blood serum of the mice in Comparative Example 4 (the mice were forcibly administered distilled water only), which confirmed the neutral fat-lowering effect of Pioglitazone. In addition, the serum neutral fat levels of the mice in Example 4 (the mice were forcibly administered the preparation prepared using the strain R037 in Preparation 1) and the mice in Reference Examples 11 to 13 were decreased similarly to that of the mice in Reference Example 10. In particular, the strain R037 in Preparation 1 showed an excellent serum neutral fat-lowering function.

These results demonstrated that the preparation prepared using the lactic acid bacterium (strain R037) of Preparation 1 has a neutral fat-lowering effect and that this effect is better than those of the other lactic acid bacteria preparations.

The invention claimed is:

1. A method for lowering neutral fat in blood of a hypertriglyceridemia patient or an individual at high risk of hypertriglyceridemia, comprising administering a strain of a lactic acid bacterium *Pediococcus acidilactici* R037 (NITE BP-900) or a product obtained from the lactic acid bacterium by grinding or disrupting or a treated product that has been subjected to at least one treatment selected from the group consisting of concentration, conversion into a paste, drying and dilution of the lactic acid bacterium, in a single dose or multiple doses such that a daily intake of the lactic acid bacterium or the product obtained from the lactic acid bacterium by a target adult person is 0.01 to 1000 mg/kg body weight per day.

2. The method according to claim 1, wherein the daily intake of the lactic acid bacterium or the product obtained from the lactic acid bacterium by the target adult person is 0.1 to 500 mg/kg body weight per day.

3. The method according to claim 1, wherein the composition is in the form of a food and the amount of the lactic acid bacterium *Pediococcus acidilactici* R037 (NITE BP-900) or the product obtained from the lactic acid bacterium is 0.001 to 50% by weight of the food.

4. The method according to claim 1, wherein the composition further comprises an excipient.

5. The method according to claim 4, wherein the amount of the excipient in the composition is 33 to 90% by weight.

6. The method according to claim 2, wherein the composition further comprises an excipient.

7. The method according to claim 6, wherein the amount of the excipient in the composition is 33 to 90% by weight.

8. The method according to claim 3, wherein the composition further comprises an excipient.

9. The method according to claim 8, wherein the amount of the excipient in the composition is 33 to 90% by weight.

* * * * *